United States Patent [19]

Canich et al.

[11] Patent Number: 5,318,935
[45] Date of Patent: Jun. 7, 1994

[54] AMIDO TRANSITION METAL COMPOUND AND A CATALYST SYSTEM FOR THE PRODUCTION OF ISOTATIC POLYPROPYLENE

[75] Inventors: Jo Ann M. Canich, Webster; Howard W. Turner, Houston, both of Tex.

[73] Assignee: Exxon Chemical Patents Inc., Linden, N.J.

[21] Appl. No.: 922,646

[22] Filed: Jul. 30, 1992

Related U.S. Application Data

[63] Continuation of Ser. No. 634,987, Dec. 27, 1990, abandoned.

[51] Int. Cl.$^5$ .............................................. C08F 4/642
[52] U.S. Cl. ..................................... 502/117; 502/103; 502/112; 526/127; 526/160; 556/12; 556/51; 556/52
[58] Field of Search ..................... 502/103, 112, 117

[56] References Cited

U.S. PATENT DOCUMENTS

| | | | |
|---|---|---|---|
| 3,392,160 | 7/1968 | Orzechowski | 502/103 X |
| 3,663,635 | 5/1972 | Lassau et al. | 502/103 X |
| 4,203,866 | 5/1980 | Corbellini et al. | 502/113 |
| 4,314,911 | 2/1982 | Giannini et al. | 502/120 X |
| 4,552,982 | 6/1985 | Ewen . | |
| 4,774,301 | 9/1988 | Campbell et al. | 502/117 X |
| 4,794,096 | 12/1988 | Ewen . | |
| 4,892,914 | 1/1990 | Hefner | 502/117 X |
| 4,956,323 | 9/1990 | Hefner | 502/103 X |

FOREIGN PATENT DOCUMENTS

| | | |
|---|---|---|
| 0349886A2 | 1/1990 | European Pat. Off. . |
| 3443087A1 | 5/1986 | Fed. Rep. of Germany . |

OTHER PUBLICATIONS

Annals of the New York Academy of Sciences, vol. 295, pp. 110–126 (1977).
J. A. Ewen, J. Am. Chem. Soc. vol. 106, pp. 6355–6364 (1984).
Kaminsky et al., Angew. Chem. Int. Ed. Engl. vol. 24, No. 6, pp. 507–508 (1985).
Wild et al., Jour. of Organomet. Chem., vol. 232, pp. 233–247 (1982).
R. A. Anderson, Inorganic Chemistry, vol. 18, No. 10, pp. 2928–2932 (1979).

Primary Examiner—Patrick P. Garvin
Attorney, Agent, or Firm—Evan K. Butts

[57] ABSTRACT

Certain bridged and unbridged amido transition metal compounds of the Group IV-B metals are disclosed. These compounds may be used in a catalyst system comprising the amido transition metal compound and an alumoxane. Also disclosed is a process using the catalyst system for the production of high molecular weight polyolefins and, particularly, high molecular weight isotactic polypropylene.

14 Claims, No Drawings

AMIDO TRANSITION METAL COMPOUND AND A CATALYST SYSTEM FOR THE PRODUCTION OF ISOTATIC POLYPROPYLENE

This is a continuation of application Ser. No. 07/634,987, filed Dec. 27, 1990 now abandoned.

FIELD OF THE INVENTION

This invention relates to certain bridged and unbridged amido transition metal compounds of the Group IV-B metals, to a catalyst system comprising an amido transition metal compound and an alumoxane, and to a process using the catalyst system for the production of high molecular weight polyolefins and, particularly, high molecular weight isotactic polypropylene.

BACKGROUND OF THE INVENTION

The various compounds that are derived from the polymerization of α-olefins show huge differences in their chemical and physical properties. These differences reflect differences in molecular structure, some of which are inherent in the use of a particular monomer or monomer combination, and some of which result from a pattern, or lack thereof, in how the monomers are combined. It is inherent that polymers of α-olefins having 3 or more carbon atoms will have pendant hydocarbyl groups attached to the polymer backbone chain. However, the stereochemical arrangement of these hydrocarbyl groups is a consequence of the interaction of monomer, catalyst and coordinated polymer during polymerization. Any pendant hydrocarbyl group may be said to lie on one side of a plane defined by the carbon atoms of the polymer backbone in an idealized elongated configuration.

As previously alluded to, the physical properties exhibited by a particular olefin polymer of a particular molecular weight are determined in major part by the arrangement of these hydrocarbyl groups along the polymer backbone. Strong polymers tend to be stereochemically regular, meaning the adjacent hydrocarbyl groups reside on the same side of the polymer backbone or switch at fairly regular intervals. Either arrangement facilitates crystalization thus lending ridgidity and strength to the the solidified polymer.

Other critical determinants of the properties which a polymer will exhibit are the type and relative concentration of monomers and comonomers, the weight average molecular weight ($M_w$) of the polymer molecules comprising the resin bulk, the molecular weight distribution (MWD) and the composition distribution of the resin. For end use applications which require high strength and low creep, the $M_w$ of such a resin must generally be in excess of 100,000.

Five types of stereoregularity, or tacticity, have been characterized: atactic, normal isotactic, isotactic stereoblock, syndiotactic, and hemiisotactic. Although all of these stereoregular configurations have been primarily demonstrated in the case of polypropylene, in theory each is equally possible for polymers comprised of any olefin, cyclic olefin or internal olefin, having 3 or more carbon atoms.

Atactic polyolefins are those wherein the hydrocarbyl groups pendent to the polymer molecule backbone assume no regular order in space with reference to the backbone. This random structure is represented by a polymer backbone of alternating methylene and methine carbons, with randomly oriented branches substituting the methine carbons. The methine carbons randomly have R and S configurations, creating adjacent pairs either of like configuration (a "meso" or "m" dyad) or of unlike configuration (a "racemic" or "r" dyad). The atactic form of a polymer contains approximately equal fractions of meso and racemic dyads. Since atactic polyolefins exhibit no regular order or repeating unit configurations in the polymer chain, they are amorphous materials. Atactic polyolefins exhibit little if any crystallinity, hence they are generally unsuitable for high strength applications regardless of the weight average molecular weight of the resin.

Isotactic polyolefins are those wherein the pendent hydrocarbyl groups are ordered in space to the same side or plane of the polymer backbone chain. Using isotactic polypropylene as an example, the isotactic structure is typically described as having the pendent methyl groups attached to the ternary carbon atoms of successive monomeric units on the same side of a hypothetical plane through the carbon backbone chain of the polymer, e.g., the methyl groups are all above or below the plane as shown below.

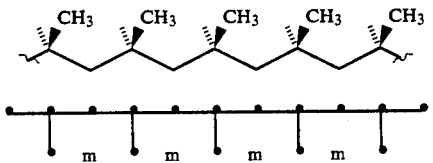

The degree of isotactic regularity may be measured by NMR techniques. Bovey's NMR nomenclature for an isotactic pentad is . . . mmmm . . . with each "m" representing a "meso" dyad or successive methyl groups on the same side in the plane.

In the normal isotactic structure of a polyolefin, all of the monomer units have the same stereochemical configuration, with the exception of random errors which appear along the polymer. Such random errors almost always appear as isolated inversions of configuration which are corrected in the very next α-olefin monomer insertion to restore the original R or S configuration of the propagating polymer chain.

The formation of stereoblock isotactic polymer differs from the formation of the normal isotactic structure in the way that the propagation site reacts to a stereochemical error in the chain. As mentioned above, the normal isotactic chain will return to the original configuration following an error because the stereochemical regulator, the catalytic active metal species and its surrounding ligands, continues to dictate the same stereochemical preference during monomer insertion. In stereoblock propagation, the catalytically active metal site itself changes from one which dictates a monomer insertion of R configuration to one which dictates an S configuration for monomer insertion. The isotactic stereoblock form is shown below.

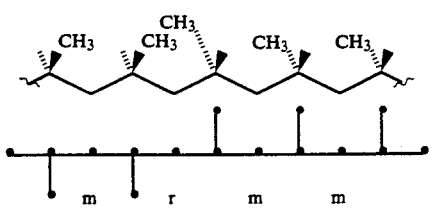

Long before anyone had discovered a catalyst system which produced the isotactic stereoblock form of a polyolefin, the possible existence of a polymer of such micro-structure had been recognized and mechanisms for its formation had been proposed based on conventional Ziegler-Natta mechanisms in Langer, A. W., *Lect. Bienn. Polym. Symp.* 7th (1974); *Ann. N.Y. Acad. Sci.* 295, 110-126 (1977). The first example of this form of polypropylene and a catalyst which produces it in a pure form were reported in U.S. Pat. No. 4,522,982.

The lengths of individual blocks of the same configuration in the stereoblock structure vary widely due to changing reaction conditions. Since only the erroneous parts of the chains affect the crystallinity of the resin product, in general, normal isotactic polymers and isotactic stereoblock polymers of long block length (greater than 50 isotactic placements) have similar properties.

Highly isotactic polyolefins exhibit a high degree of crystallinity. Accordingly, isotactic polyolefins are, depending upon their weight average molecular weight exceeding about 100,000, well suited to high strength end use applications.

Syndiotactic polyolefins are those wherein the hydrocarbyl groups pendent to the polymer molecular backbone alternate sequentially in order from one side or plane to the opposite side or plane relative to the polymer backbone, as shown below.

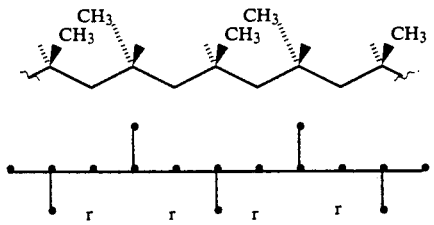

In NMR nomenclature, this segment, or pentad, is described as ... rrrr ... in which each r represents a "racemic" dyad, i.e., successive methyl groups on alternate sides of the plane. The percentage of r dyads in the chain determines the degree of syndiotacticity of the polymer. Highly syndiotactic polymers are generally highly crystalline and will frequently have high melting points similar to their isotactic polymorphs. Like isotactic polyolefins, syndiotactic polyolefins are capable of exhibiting a high degree of crystallinity, hence are suitable for high strength applications provided their $M_w$ exceeds about 100,000.

For any of the above described materials the final resin properties and its suitability for particular applications depend on the type of tacticity, the melting point, the average molecular weight, the molecular weight distribution, the type and level of monomer and comonomer, the sequence distribution, and the presence or absence of head or end group functionality. Accordingly, the catalyst system by which such a stereoregular polyolefin is to be produced should, desirably, be versatile in terms of $M_w$, MWD, tacticity type and level, and comonomer choice. Further, the catalyst system should be capable of producing these polymers with or without head and/or end group functionality, such as olefinic unsaturation. Still further, such catalyst system must be capable, as a commercially practical constraint, of producing such resins at an acceptable production rate. Most preferably, the catalyst system should be one which, at its productivity rate, provides a resin product which does not require a subsequent treatment to remove catalyst residue to a level which is acceptable for the resin in the end use application desired. Finally, an important feature of a commercial catalyst system is its adaptability to a variety of processes and conditions.

Conventional titanium based Ziegler-Natta catalysts for the preparation of isotactic polymers are well known in the art. These commercial catalysts are well suited for the production of highly crystalline, high molecular weight materials. The systems are, however, limited in terms of molecular weight, molecular weight distribution, and tacticity control. The fact that the conventional catalysts contain several types of active sites further limits their ability to control the composition distribution in copolymerization.

More recently a new method of producing isotactic polymers from an alumoxane cocatalyzed, or activated, metallocene which in its natural state has chirality centered at the transition metal of the metallocene, was reported in Ewen, J. A., *J. Amer. Chem. Soc.*, v. 106, p. 6355 (1984) and Kaminsky, W., et al., *Angew. Chem. Int. Ed. Eng.*; 24, 507-8 (1985).

Catalysts that produce isotactic polyolefins are also disclosed in U.S. Pat. No. 4,794,096. This patent discloses a chiral, stereorigid metallocene catalyst which is activated by an alumoxane cocatalyst which is reported to polymerize olefins to isotactic polyolefin forms. Alumoxane cocatalyzed metallocene structures which have been reported to polymerize stereoregularly are the ethylene bridged bis-indenyl and bis-tetrahydroindenyl titanium and zirconium (IV) catalyst. Such catalyst systems were synthesized and studied in Wild et al., *J. Organomet. Chem.* 232, 233-47 (1982), and were later reported in Ewen and Kaminsky et al., mentioned above, to polymerize α-olefins stereoregularly. Further reported in West German Off DE 3443087Al (1986), but without giving experimental verification, is that the bridge length of such stereorigid metallocenes can vary from a $C_1$ to $C_4$ hydrocarbon and the metallocene rings can be simple or bi-cyclic but must be asymmetric. In contrast to the metallocene catalysts disclosed in U.S. U.S. Pat. No. 4,794,096 and West German Patent DE 3443087Al, certain species of this invention are capable of producing a highly isotactic polymer using an achiral catalyst.

The use of transition metal based catalysts having amido groups attached to the transition metal have received some attention in polymer research. A process for producing syndiotactic polystyrene using a trisamido zirconium catalyst is disclosed in U.S. Pat. No. 4,774,301. As taught therein, the zirconium compound may be combined with an alumoxane to produce a polymerization catalyst. A syndiotactic polymer results when vinyl aromatic monomers, which have been known to yield syndiotactic polymers generally, are polymerized by a tris-amido zirconium-alumoxane catalyst.

In European Patent 349,886, titanium having bonded thereto a saturated alkyl-substituted amido group, is reported to yield an active catalyst in the presence of alumoxane. This catalyst system is capable of producing polyethylene copolymers having a high degree of structural randomness and narrow molecular weight distribution. Also reported in EP 349,886 are references to prior amide containing Group IV-B metal catalysts for the homopolymerization of ethylene, which, when applied to copolymerization, suffer from the various disadvantages of low molecular weight product, broad molecular weight distribution and low catalytic activity.

In view of the high strength and other physical properties that make stereoregular polymers desirable in applications for which other moldable plastics are ill suited and in view of the few methods currently available for producing stereoregular polymers, there is a need for a catalyst as disclosed hereinafter for producing high molecular weight, highly isotactic polymers. It is further desirable that such a catalyst have high activity so as to allow production of a polymer which is ready to be molded and/or machined for its ultimate use without treatment for removal of contaminants (catalyst residue). It is also desirable to obtain a catalyst that is useful for production of ethylene base polymers.

SUMMARY OF THE INVENTION

This invention discloses an alumoxane cocatalyzed catalyst system for the production of highly crystalline polyolefins the transition metal component of which is a bridged amido transition metal compound represented by the general formula:

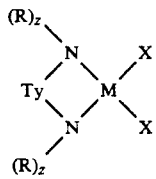

wherein: "M" is zirconium, hafnium or titanium; "N" is a nitrogen atom having three substituents; "y" is 1 or 0 denoting the presence or absence, respectively, of a bridging group T between nitrogen atoms and "z" is 2−y; "X" and "X'" are any univalent anionic ligand such as a halide, hydride, substituted or unsubstituted $C_1$-$C_{30}$ hydrocarbyl, alkoxide, aryloxide, amide, arylamide, phosphide, arylphosphide, or "X" and "X'" together are a divalent radical such as an alkylidene, cyclometallated hydrocarbyl or any other divalent anionic chelating ligand; "T" is a covalent bridging group selected from the group consisting of unsubstituted hydrocarbyls and hydrocarbyls containing a Group IV-A or VI-A element; and each "R" and "R'" is independently a radical selected from the group consisting of singly branched hydrocarbyl radicals having between 1 and 30 carbon atoms, multiple branched hydrocarbyl radicals having between 1 and 30 carbon atoms, halogen radicals, amido radicals, phosphido radicals, silyl radicals, alkoxy radicals, alkylborido radicals, $C_1$-$C_{30}$ hydrocarbyl-substituted Group IV-A metalloid radicals; and substituted $C_1$-$C_{30}$ hydrocarbyl radicals wherein one or more hydrogen atoms is replaced by a halogen radical, an amido radical, a phosphido radical, an alkoxy radical or any other radical containing a Lewis acidic or basic functionality.

Further disclosed is a polymerization process incorporating the catalyst system. The catalyst system is prepared by the combination of an amido transition metal compound and an alumoxane, and may be employed in solution, slurry, gas phase, or high pressure polymerization. The catalyst may also be prepared in the supported form. The catalyst system of this invention polymerizes propylene to high molecular weight, highly isotactic polypropylene, in addition to homopolymerizing ethylene and copolymerizing ethylene or propylene with α-olefins, cyclic olefins, dienes or other unsaturated monomers.

DESCRIPTION OF THE PREFERRED EMBODIMENT

A. Transition Metal Component

The Group IV-B transition metal component of the catalyst system is represented by the general formula:

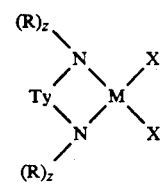

wherein the letter symbols have the following meanings:

"M" is zirconium, titanium or hafnium;

"N" is a nitrogen atom having three substituent groups;

"y" is 1 or 0 denoting the presence or absence, respectively, of a bridging group T between nitrogen atoms and "z" is 2−y;

each "R" is independently a radical selected from the group consisting of singly branched hydrocarbyl radicals having between 1 and 30 carbon atoms, preferably between 3 and 30 carbon atoms; multiply branched hydrocarbyl radicals having between 1 and 30 carbon atoms, preferably between 3 and 30 carbon atoms; halogen radicals; amido radicals; phosphido radicals; silyl radicals; alkoxy; and alkylborido radicals; substituted $C_1$-$C_{30}$ hydrocarbyl radicals wherein one or more hydrogen atoms is replaced by a halogen radical, an amido radical, a phosphido radical, an alkoxy radical or any other radical containing a Lewis acidic or basic functionality; $C_1$-$C_{30}$ hydrocarbyl-substituted metalloid radicals wherein the metalloid is selected from the Group IV-A of the Periodic Table of Elements;

each "X" is independently any univalent anionic ligand such as a halide, hydride, or substituted or unsubstituted $C_1$-$C_{20}$ hydrocarbyl, alkoxide, aryloxide, amide, arylamide, phosphide, arylphosphide or both "X" and "X'" together are an alkylidene, a cyclometallated hydrocarbyl or any other divalent anionic chelating ligand; more particularly, X may be a ligand of the general formula $N(R)_2$ wherein R has the same meaning previously ascribed to it; most particularly, X may be a silylamide of the general formula $N[Si(R)_3]_2$;

T is a covalent bridging group containing a Group IV-A or VI-A element such as, but not limited to, a dialkyl, alkylaryl or diaryl silicon radical; a dialkyl, alkylaryl or diaryl germanium radical; alkyl or aryl phosphine; alkyl or aryl amine radical; an oxygen or sulfur radical; or a hydrocarbyl radical having 1 or more carbon atoms such as methylene, ethylene and the like.

Specific, nonlimiting examples of the T group which are suitable as a constituent group of the Group IV-B transition metal component of the catalyst system are dimethylsilyl, diethylsilyl, di-n-propylsilyl, diisopropylsilyl,di-n-butylsilyl,di-t-butylsilyl,di-n-hexylsilyl, methylphenylsilyl, ethylmethylsilyl, diphenylsilyl, di(p-t-butylphenethylsilyl), n-hexylmethylsilyl, cyclopentamethylenesilyl, cyclotetramethylenesilyl, cyclotrimethylenesilyl, dimethylgermanyl, diethylgermanyl, methylene, dimethylmethylene, diethylmethylene, ethylene, dimethylethylene, diethylethylene, dipropylethylene, propylene, dimethylpropylene, diethylpropylene, 1,1-dimethy-3-3-dimethylpropylene, tetramethyldisiloxane, 1,1,4,4-tetramethyldisilylethylene, oxygen and sulfur.

Exemplary hydrocarbyl radicals for X are methyl, ethyl, propyl, isopropyl, butyl, amyl, isoamyl, hexyl, isobutyl, heptyl, octyl, nonyl, decyl, cetyl, 2-ethylhexyl, phenyl and the like, with methyl being preferred. Exemplary halogen atoms for X include chlorine, bromine, fluorine and iodine, with chlorine being preferred. Exemplary alkoxides and aryloxides for X are methoxide, ethoxide, propoxide, butoxide, phenoxide and substituted phenoxides such as 4-methylphenoxide. Exemplary amides of X are dimethylamide, diethylamide, methylethylamide, di-t-butylamide, diisoproylamide and the like. Exemplary aryl amides are diphenylamide and any other substituted phenyl amides. Exemplary silyl amides are di-trimethylsilylamide, di-triethylsilylamide and triethyl-trimethyl silylamide, with di-trimethylsilylamide being preferred. Exemplary phosphides of X are diphenylphosphide, dicyclohexylphosphide, diethylphosphide, dimethylphosphide and the like. Exemplary alkyldiene radicals for both X's together are methylidene, ethylidene, propylidene, or the dianion of ethyleneglycol and the like.

Suitable hydrocarbyl and substituted hydrocarbyl radicals for the R group will contain from 1 to about 30 carbon atoms and include singly and multiply branche alkyl radicals, cyclic hydrocarbon radicals, alkyl-substituted cyclic hydrocarbon radicals, aromatic radicals and alkyl-substituted aromatic radicals, amido-substituted hydrocarbon radicals, phosphido-substituted hydrocarbon radicals, alkoxy-substituted hydrocarbon radicals, and halo-substituted hydrocarbon radicals or hydrocarbon radicals containing substitutions by any Lewis basic or acidic functional group. Suitable organometallic radicals for the R group include trimethylsilyl, triphenylsilyl, triphenylgermyl, trimethylgermyl and the like. Other suitable radicals for the R group include amido radicals, phosphido radicals, alkoxy radicals, alkyl boride radicals and the like. Of the suitable R groups the organometalic radicals of silicon such as trimethylsilyl, triethylsilyl, ethyldimethylsilyl and methyldiethylsilyl are preferred; the most preferred being trimethylsilyl.

A number of final components may be formed by permuting all possible combinations of the constituent moieties with each other. Illustrative transition metal compounds are: bis(di-trimethylsilylamido) zirconium dichloride, bis(di-isobutylamido) hafnium dimethyl, bis(di-tertbutylamido)zirconium dichloride, (di-cyclohexylamido)(di-trimethylsilylamido) titanium dihydride, tris(di-trimethylsilylamido) zirconium chloride,tris(di-triphenylgermylamido) hafniumchloride, and tetrakis(di-trimethylsilylamido) zirconium.

The Group IV-B metal compounds have been used to produce isotactic polypropylene of high stereoregularity. As demonstrated in example 9, when the achiral compound bis(di-trimethylsilylamido) zirconium dichloride is combined with alumoxane to form a catalyst system, that system is capable of producing isotactic polypropylene having fewer than 50 chain defects per 1000 monomer units. The preparation of compounds of this type are well known in the literature and include references such as R. A. Anderson, *Inorganic Chemistry* (1979), 18, 2928.

B. Alumoxane Component

The alumoxane component of the catalyst system is an oligomeric compound which may be represented by the general formula $(R^3-Al-O)_m$ which is a cyclic compound, or may be $R^4(R^5-Al-O-)_m-AlR_2^6$ which is a linear compound. An alumoxane is generally a mixture of both the linear and cyclic compounds. In the general alumoxane formula $R^3$, $R^4$, $R^5$ and $R^6$ are, independently a $C_1-C_5$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes which may be utilized in the catalyst systems of this invention are those prepared by the hydrolysis of a trialkylaluminum or haloalkylaluminum; such as trimethylaluminum, triethyaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

C. Catalyst System

The catalyst systems employed in the invention comprise a complex formed upon admixture of the amido Group IV-B transition metal component with an alumoxane component. The catalyst system may be prepared by addition of the requisite bis-amido Group IV-B transition metal and alumoxane components to an inert solvent in which olefin polymerization can be carried out by a solution, slurry or bulk phase polymerization procedure.

The catalyst system may be conveniently prepared by placing the selected amido Group IV-B transition metal component and the selected alumoxane component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention optimum results are generally obtained wherein the amido Group IV-B transition metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Sufficient solvent should be employed so as to provide adequate heat transfer away from the catalyst components during reaction and to permit good mixing.

The catalyst system ingredients—that is, the amido Group IV-B transition metal, the alumoxane, and polymerization diluent—can be added to the reaction vessel rapidly or slowly. The temperature maintained during the contact of the catalyst components can vary widely, such as, for example, from −10° to 300° C. Greater or lesser temperatures can also be employed. Preferably, during formation of the catalyst system, the reaction is maintained within a temperature of from about 25° to 100° C., most preferably about 25° C.

At all times, the individual catalyst system components, as well as the catalyst system once formed, are protected from oxygen and moisture. Therefore, the reactions to prepare the catalyst system are performed in an oxygen and moisture free atmosphere and, where the catalyst system is recovered separately it is recovered in an oxygen and moisture free atmosphere. Preferably, therefore, the reactions are performed in the presence of an inert dry gas such as, for example, helium or nitrogen.

C. Polymerization Process

In a preferred embodiment of the process of this invention the catalyst system is utilized in the liquid phase (slurry, solution, suspension or bulk phase or combination thereof), high pressure fluid phase or gas phase polymerization of an olefin monomer. These processes may be employed singularly or in series. The liquid phase process comprises the steps of contacting an olefin monomer with the catalyst system in a suitable polymerization diluent and reacting said monomer in the presence of said catalyst system for a time and at a temperature sufficient to produce a polyolefin of high molecular weight.

The monomer for such process may comprise propylene alone, for the production of a isotactic polypropylene. Conditions most preferred for the production of isotactic polypropylene are those wherein propylene is submitted to the reaction zone at pressures of from about 0.019 psi to about 50,000 psi and the reaction temperature is maintained at from about −100° to about 300° C. The aluminum to transition metal molar ratio is preferably from about 1:1 to 20,000:1. A more preferable range would be 1:1 to 2000:1. The reaction time is preferably from about 1 hour to about 6 hours.

The monomer may also comprise ethylene alone, for the production of homopolyethylene, or ethylene in combination with an α-olefin having 3 to 20 carbon atoms for the production of an ethylene-α-olefin copolymer. Homopolymers of higher α-olefin such as butene and copolymers thereof with ethylene and/or $C_4$ or higher α-olefins and diolefins can also be prepared. Conditions most preferred for the homo- or copolymerization of ethylene are those wherein ethylene is submitted to the reaction zone at pressures of from about 0.019 psi to about 50,000 psi and the reaction temperature is maintained at from about −100° to about 300° C. The aluminum to transition metal molar ratio is preferably from about 1:1 to 20,000:1. A more preferable range would be 1:1 to 2000:1. The reaction time is preferably from about 10 seconds to about 1 hour.

Without limiting in any way the scope of the invention, one means for carrying out the process of the present invention for production of a copolymer is as follows: in a stirred-tank reactor, liquid α-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid α-olefin comonomer, together with dissolved ethylene gas, and a vapor phase containing vapors of all monomers. The reactor temperature and pressure may be controlled via reflux of vaporizing α-olefin monomer (autorefrigeration), as well as by cooling coils, jackets etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

EXAMPLES

Example 1

The polymerization run was performed in a 1-liter autoclave reactor equipped with a paddle stirrer, an external water jacket for temperature control, a regulated supply of dry nitrogen, ethylene, propylene, 1-butene and hexane, and a septum inlet for introduction of other solvents or comonomers, transition metal compound and alumoxane solutions. The reactor was dried and degassed thoroughly prior to use. A typical run consisted of injecting 400 ml of toluene, 5 ml 1.0 M MAO, 0.27 mg of $[(Me_3Si)_2N]_2ZrCl_2$ (0.2 ml of a 13.5 mg in 10 ml of toluene solution) into the reactor. The reactor was then heated to 80° C. and the ethylene (60 psi) was introduced into the system. The polymerization reaction was limited to 10 minutes. The reaction was ceased by rapidly cooling and venting the system. The solvent was evaporated off of the polymer by a stream of nitrogen. Polyethylene was recovered (7.4 g, MW=315,000, MWD=2.261).

Example 2

Using the same reactor design and general procedure as example 1, 400 ml of toluene, 5.0 ml of 1.0 M MAO, and 0.32 of mg of [(Me$_3$Si)$_2$N]$_2$HfCl$_2$ (0.2 ml of a 1.60 mg in for 10 ml of toluene solution) were added to the reactor. The reactor was heated at 80° C., the ethylene was introduced (60 psi), and the reaction was allowed to run for 10 minutes, followed by rapidly cooling and venting the system. After evaporation of the toluene, 2.7 g of polyethylene was recovered (MW=267,200, MWD=2.122).

Example 3

Using the same reactor design and general procedure as example 1, 300 ml of toluene, 100 ml of propylene, 7.0 ml of 1.0 M MAO, and 1.35 mg of [(Me$_3$Si)$_2$N]$_2$ZrCl$_2$ (1 ml of a 13.5 in 10 ml of toluene solution) were added the reactor. The reactor was heated at 50° C., the ethylene was introduced (65 psi), and the reaction was allowed to run for 30 minutes, followed by rapidly cooling and venting the system. After evaporation of the toluene, 9.3 g of an ethylene-propylene copolymer was recovered (MW=131,000, MWD=1.837, 121.7 short chain branches (SCB)/1000C by IR).

EXAMPLE 4

Using the same reactor design and general procedure as example 1, 300 ml of toluene, 100 ml of propylene, 7.0 ml of 1.0 M MAO, and 1.6 mg of [(Me$_3$Si)$_2$N]HfCl$_2$ (1 ml of a 16 mg in 10 ml of toluene solution) were added to the reactor. The reactor was heated at 80° C., the ethylene was introduced (60 psi), and the reaction was allowed to run for 30 minutes, followed by rapidly cooling and venting the system. After evaporation of the toluene, 8.2 g of an ethylene-propylene copolymer was recovered (MW=80,700, MWD=1.537, 89.3 SCB/1000C by IR).

Example 5

Using the same reactor design and general procedure as example 1, 300 ml of toluene, 100 ml of 1-butene, 7.0 ml of 1.0 M MAO, and 1.35 mg of [(Me$_3$Si)$_2$N]$_2$ZrCl$_2$ (1 ml of a 13.5 mg in 10 ml of toluene solution) were added to the reactor. The reactor was heated at 80° C., the ethylene was introduced (60 psi), and the reaction was allowed to run for 30 minutes, followed by rapidly cooling and venting the system. After evaporation of the toluene, 4.3 g of an ethylene-butene copolymer was recovered (MW=91,100, MWD=1.643, 51.4 SCB/1000C by $^{13}$C NMR).

Example 6

Using the same reactor design and general procedure as example 1, 300 ml of toluene, 100 ml of 1-butene, 7.0 ml of 1.0 M MAO, and 1.6 mg of [(Me$_3$Si)$_2$N]$_2$HfCl$_2$ (1 ml of a 16 mg of 10 ml of toluene solution) were added to the reactor. The reactor was heated at 80° C., the ethylene was introduced (60 psi), and the reaction was allowed to run for 30 minutes, followed by rapidly cooling and venting the system. After evaporation of the toluene, 9.3 g of an ethylene-butene copolymer was recovered (MW=70,800, MWD=1.710, 46.8 SCB1000C by $^{13}$C NMR).

Example 7

Using the same reactor design and general procedure as example 1, 300 ml of toluene, 100 ml of 1-hexene, 7.0 ml of 1.0 M MAO, and 1.35 mg of [(Me$_3$Si)$_2$N]$_2$ZrCl$_2$(1 ml of a 13.5 mg in 10 ml of toluene solution) were added to the reactor. The reactor was heated at 80° C., the ethylene was introduced (60 psi), and the reaction was allowed to run for 30 minutes, followed by rapidly cooling and venting the system. After evaporation of the toluene, 13.9 g of an ethylene-hexene copolymer was recovered (MW=111,200, MWD=1.782, 32.2 SCB/1000C by IR).

Example 8

Using the same reactor design and general procedure as example 1, 300 ml of toluene, 100 ml of 1-hexene, 7.0 ml of 1.0 M MAO, and 1.6 mg of [(Me$_3$Si)$_2$N]$_2$HfCl$_2$ (1 ml of a 16.0 mg in 10 ml of toluene solution) were added to the reactor. The reactor was heated at 50° C., the ethylene was introduced (65 psi), and the reaction was allowed to run for 30 minutes, followed by rapidly cooling and venting the system. After evaporation of the toluene, 8.7 g of an ethylene-hexene copolymer was recovered (MW=236,700, MWD=1.780, 20.1 SCB/1000C by IR).

Example 9

Using the same reactor design and general procedure as example 1, 100 ml of toluene, 200 ml of propylene, 10.0 ml of 1.0 M MAO, and 8.3 mg of [(Me$_3$Si)$_2$N]$_2$ZrCl$_2$ in 10 ml toluene were added to the reactor. The reactor was heated at 30° C. and the reaction was allowed to run for 3 hours, followed by rapidly cooling and venting the system. After evaporation of the toluene, 3.2 g of isotactic polypropylene was recovered (MW=95,500, MWD=1.758, 90% (m) isotactic with 40 chain defects per 1000 monomer units as determined by $^{13}$C NMR, 146° C. mp).

Example 10

The polymerization was performed in a stirred 100 ml stainless steel autoclave which was equipped to perform polymerizations at temperatures up to 300° C. and pressures up to 2500 bar. the reactor was evacuated, purged with nitrogen, purged with ethylene and heated to 202° C. The comonomer, 1-hexene (75 ml), was added to the reactor under ethylene pressure. A stock solution of [(Me$_3$Si)$_2$N]$_2$ZrCl$_2$ was prepared by dissolving 7.6 mg of the transition metal compound in 25 ml of toluene. The test solution was prepared by adding 2.5 ml of the stock solution to 10.0 ml of a 1.0 M MAO solution. The test solution (0.43 ml) was transferred by nitrogen pressure into a constant-volume injection tube. The autoclave was pressurized with ethylene to 1792 bar and was stirred at 1800 rpm. The test solution (0.43 ml) was injected into the autoclave with excess pressure, at which time a temperature rise of 9° C. was observed. The temperature and pressure were recorded continuously for 120 seconds, at which time the contents of the autoclave were rapidly vented into a receiving vessel. The reactor was washed with xylene to recover any polymer remaining within. These washings were combined with the polymer released when the reactor was vented. Precipitation of the polymer from the mixture by addition of acetone yielded 1.3 g of an ethylene-hexene copolymer (MW=42,000, MWD=2.07, 8.9 SCB/1000C by IR)

Example 11

Using the same reactor design as described in example 10, the reactor was evacuated, purged with nitrogen, purged with ethylene and heated to 199° C. The comonomer 1-hexene (75 ml), was added to the reactor under ethylene pressure. A stock solution of [(Me$_3$Si)$_2$N]$_2$HfCl$_2$ was prepared by dissolving 9.0 mg of the transition metal compound in 25 ml of toluene. The test solution was prepared by adding 2.5 ml of the stock solution to 10.0 ml of a 1.0 M MAO solution. The test solution (0.43 ml) was transferred by nitrogen pressure into a constant-volume injection tube. The autoclave was pressurized with ethylene to 1831 bar and was stirred at 1800 rpm. The test solution was injected into the autoclave with excess pressure, at which time a temperature rise of 7° C. was observed. The temperature and pressure were recorded continuously for 120 seconds, at which time the contents of the autoclave were rapidly vented into a received vessel. The reactor was washed with xylene to recover any polymer remaining within. These washings were combined with the polymer released when the reactor was vented. Precipitation of the polymer from the mixture by addition of acetone yielded 0.5 g of an ethylene-hexene copolymer (MW=57,000, MWD=2.22, 8.0 SCB/1000C by IR).

The invention has been described with reference to its preferred embodiments. Those of ordinary skill in the art may, upon reading this disclosure, appreciate changes or modifications which do not depart from the scope and spirit of the invention as described above or claimed hereafter.

We claim:

1. A catalyst system for the polymerization of α-olefins comprising the reaction product of:
  a) a Group IV-B metal compound of the general formula:

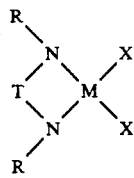

wherein: "M" is zirconium, hafnium or titanium; "N" is a nitrogen atom having three substituents; each "X" is independently, any univalent anionic ligand selected from the group consisting of halide, hydride, straight, branched, or aromatic hydrocarbyl radicals, alkoxide, aryloxide, amides having singly or multiply branched hydrocarbyl radicals having between 3 and 30 carbon atoms or, arylamide, phosphide and arylphosphide; "T" is a covalent bridging group selected from the group consisting of unsubstituted hydrocarbyls and substituted hydrocarbyls containing a Group IV-A or VI-A element; and each "R" is independently a radical selected from the group consisting of singly branched hydrocarbyl radicals having between 4 and 30 carbon atoms, multiply branched hydrocarbyl radicals having between 4 and 30 carbon atoms, halogen radicals, amido radicals, phosphido radicals, silyl radicals, alkoxy radicals, alkylborido radicals, C$_1$-C$_{30}$ hydrocarbyl-substituted Group IV-A metalloid radicals; and substituted C$_1$-C$_{30}$ hydrocarbyl radicals wherein one or more hydrogen atoms is replaced by a halogen radical, an amido radical, a phosphido radical, alkoxy radical or any other radical containing a Lewis acidic or basic functionality; and
  b) an alumoxane.

2. The catalyst system of claim 1 wherein each R is independently a radical selected from the group consisting of halogen radicals, amido radicals, phosphido radicals, silyl radicals, alkoxy radicals, alkylborido radicals, C$_1$-C$_{30}$ hydrocarbyl-substituted Group IV-A metalloid radicals; and substituted C$_1$-C$_{30}$ hydrocarbyl radicals wherein one or more hydrogen atoms is replaced by a halogen radical, an amido radical, a phosphido radical, an alkoxy radical or any other radical containing a Lewis acidic or basic functionality.

3. The catalyst system of claim 1 wherein each X is independently selected from the group consisting of hydrides, alkoxides, amides, hydrocarbyls and halides.

4. A catalyst system for the polymerization of α-olefins comprising the reaction product of:
  a) a Group IV-B metal compound of general formula:

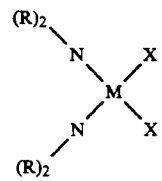

wherein: "M" is zirconium, hafnium or titanium, "N" is a nitrogen atom having three substituents; each "X" is, independently, any univalent anionic ligand selected from the group consisting of halide, hydride, straight, branched, or aromatic hydrocarbyl radicals alkoxide, aryloxide, amides having singly or multiply branched hydrocarbyl radicals having between 3 and 30 carbon atoms, arylamide, phosphide or arylphosphide; and each "R" is independently a hydrocarbyl substituted radical of silicon or metals of group IV A metal, or a radical containing a Lewis acidic or basic functionality; and
  b) an alumoxane.

5. The catalyst system of claim 1 or 4 wherein the alumoxane is derived from the hydrolysis of an alumalkyl selected from the group consisting of trimethyl aluminum, triethylaluminum, and triisobutylaluminum.

6. The catalyst system of claim 5 wherein "M" is zirconium or hafnium.

7. The catalyst system of claim 4 wherein each R is independently a radical selected from the group consisting of trimethylsilyl, triethylsilyl, ethyldimethylsilyl, and methyldiethylsilyl.

8. The catalyst system of claim 4 wherein each X is independently selected from the group consisting of hydrides, alkoxides, amides, hydrocarbyls and halides.

9. The catalyst system of claim 4 wherein the alumoxane is derived from the hydrolysis of an alumalkyl selected from the group consisting of trimethyl aluminum, triethylaluminum, and triisobutylaluminum.

10. The catalyst system of claim 9 wherein "M" is zirconium of hafnium.

11. A catalyst system for the polymerization of α-olefins comprising, as a component:
  a) a Group IV-B metal compound of the general formula:

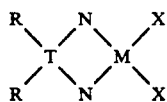

wherein: "M" is zirconium, hafnium or titanium; "N" is a nitrogen atom having three substituents; each "X" is independently, any univalent anionic ligand selected from the group consisting of halide, hydride, straight, branched, or aromatic hydrocarbyl radicals, alkoxide, aryloxide, amides having singly or multiply branched hydrocarbyl radicals having between 3 and 30 carbon atoms or, arylamide, phosphide and arylphosphide; "T" is a covalent bridging group selected from the group consisting of unsubstituted hydrocarbyls and substituted hydrocarbyls containing a Group IV-A or VI-A element; and each "R" is independently a radical selected from the group consisting of singly branched hydrocarbyl radicals having between 4 and 30 carbon atoms, multiply branched hydrocarbyl radicals having between 4 and 30 carbon atoms, halogen radicals, amido radicals, phospido radicals, silyl radicals, alkoxy radicals, alkylborido radicals; $C_1$–$C_{30}$ hydrocarbyl-substituted Group IV-A metalloid radicals; and substituted $C_1$–$C_{30}$ hydrocarbyl radicals wherein one or more hydrogen atoms is replaced by a halogen radical, an amido radical, a phospido radical, alkoxy radical or any other radical containing a Lewis acidic or basic functionality.

12. A catalyst system for the polymerization of α-olefins comprising, as a component:
Group IV-B metal compound of general formula:

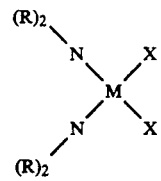

wherein: "M" is zirconium, hafnium, or titanium, "N" is a nitrogen atom having three substituents; each "X" is, independently, any univalent anionic ligand selected from the group consisting of halide, hydride, straight, branched, or aromatic hydrocarbyl radicals alkoxide, aryloxide, amides having singly or multiply branched hydrocarbyl radicals having between 3 and 30 carbon atoms, arylamide, phosphide or arylphosphide; and each "R" is independently a hydrocarbyl substituted radical of silicon or metals of Group IV A or a radical containing a Lewis acidic or basic functionality.

13. The catalyst system of claim 11 in supported form.

14. The catalyst system of claim 12 in supported form.

* * * * *